(12) United States Patent
Walzman (10) Patent No.: US 10,543,015 B2
(45) Date of Patent: *Jan. 28, 2020

(54) MESH DISC FOR SACCULAR ANEURYSMS AND COVER FOR SACCULAR OUT-POUCHING

(71) Applicant: Daniel Ezra Walzman, Bergenfield, NJ (US)

(72) Inventor: Daniel Ezra Walzman, Bergenfield, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/732,519

(22) Filed: Nov. 20, 2017

(65) Prior Publication Data

US 2018/0153556 A1 Jun. 7, 2018

Related U.S. Application Data

(60) Provisional application No. 62/497,851, filed on Dec. 5, 2016, provisional application No. 62/600,134, filed on Feb. 13, 2017.

(51) Int. Cl.
*A61B 17/3207* (2006.01)
*A61B 17/12* (2006.01)
(Continued)

(52) U.S. Cl.
CPC .. *A61B 17/320758* (2013.01); *A61B 17/1214* (2013.01); *A61B 17/1219* (2013.01); *A61B 17/12031* (2013.01); *A61B 17/12113* (2013.01); *A61B 17/12172* (2013.01); *A61B 17/12177* (2013.01); *A61F 2/852* (2013.01); *A61F 2/91* (2013.01); *A61L 29/145* (2013.01); *A61L 31/022* (2013.01); *A61L 31/04* (2013.01); *A61L 31/10* (2013.01); *A61L 31/125* (2013.01); *A61L 31/14* (2013.01); *A61L 31/145* (2013.01); *A61L 31/146* (2013.01); *A61L 31/16* (2013.01); *A61B 17/12122* (2013.01); *A61B 17/22032* (2013.01); *A61B 2017/00477* (2013.01); *A61B 2017/00867* (2013.01); *A61B 2017/00893* (2013.01); *A61B 2017/00898* (2013.01); *A61B 2017/1205* (2013.01); *A61B 2017/1209* (2013.01); *A61B 2017/320716* (2013.01); *A61B 2090/3966* (2016.02); *A61B 2217/005* (2013.01); *A61B 2217/007* (2013.01); *A61F 2002/823* (2013.01); *A61F 2002/826* (2013.01); *A61F 2220/0033* (2013.01); *A61F 2250/0063* (2013.01); *A61L 29/16* (2013.01); *A61L 2430/06* (2013.01);
(Continued)

(58) Field of Classification Search
CPC ........ A61B 17/12109; A61B 17/12031; A61B 17/1214; A61B 17/12113; A61B 17/12172; A61B 17/12; A61B 17/12177
USPC ....................................................... 606/200
See application file for complete search history.

(56) References Cited

U.S. PATENT DOCUMENTS 3,874,388 A 4/1975 King et al.
4,282,875 A 8/1981 Serbinenko
(Continued)

FOREIGN PATENT DOCUMENTS

WO WO2011/057002 A2 5/2011

*Primary Examiner* — George J Ulsh (57) ABSTRACT

The present invention teaches the uses of a disc shaped mesh intrasaccular occlusion structure, with optional supplemental hydrogel, which is designed to implement an endovascular treatment to facilitate saccular aneurysm treatment while ameliorating or eliminating aneurysm recurrence.

18 Claims, 6 Drawing Sheets

(51) Int. Cl.
*A61L 29/14* (2006.01)
*A61L 31/10* (2006.01)
*A61L 31/16* (2006.01)
*A61L 31/14* (2006.01)
*A61F 2/852* (2013.01)
*A61F 2/91* (2013.01)
*A61L 31/02* (2006.01)
*A61L 31/04* (2006.01)
*A61L 31/12* (2006.01)
*A61M 25/00* (2006.01)
*A61L 29/16* (2006.01)
*A61B 17/22* (2006.01)
*A61B 17/00* (2006.01)
*A61B 90/00* (2016.01)
*A61F 2/82* (2013.01)
*A61M 25/10* (2013.01)

(52) U.S. Cl.
CPC ..... *A61M 25/10* (2013.01); *A61M 2025/0057* (2013.01); *A61M 2210/125* (2013.01)

(56) References Cited

U.S. PATENT DOCUMENTS

| | | |
|---|---|---|
| 4,346,712 A | 8/1982 | Handa et al. |
| 4,402,319 A | 9/1983 | Handa et al. |
| 4,619,246 A | 10/1986 | Molgaard-Nielsen et al. |
| 4,675,361 A | 6/1987 | Ward, Jr. |
| 4,921,478 A * | 5/1990 | Solano ............... A61M 25/104 604/103.07 |
| 5,165,421 A | 11/1992 | Fleischhacker et al. |
| 5,263,963 A | 11/1993 | Garrison et al. |
| 5,334,210 A | 8/1994 | Gianturco |
| 5,733,294 A | 3/1998 | Forber et al. |
| 5,907,893 A | 6/1999 | Zadno-Azizi et al. |
| 6,221,086 B1 | 4/2001 | Forber |
| 6,375,670 B1 | 4/2002 | Greenhalgh |
| 6,605,102 B1 | 8/2003 | Mazzocchi et al. |
| 7,575,582 B2 | 8/2009 | Gandhi et al. |
| 2002/0173835 A1* | 11/2002 | Bourang ............... A61F 2/954 623/1.11 |
| 2004/0087998 A1* | 5/2004 | Lee ................... A61B 17/12022 606/200 |
| 2005/0159645 A1* | 7/2005 | Bertolero ........... A61B 1/00142 600/116 |
| 2006/0293612 A1* | 12/2006 | Jenson ............... A61B 17/3207 600/585 |
| 2007/0078480 A1* | 4/2007 | Belenkaya ....... A61B 17/12022 606/200 |
| 2008/0033341 A1 | 2/2008 | Grad |
| 2010/0069948 A1 | 3/2010 | Veznedaroglu et al. |
| 2010/0087709 A1* | 4/2010 | Bertolero ........... A61B 1/00142 600/116 |
| 2011/0144669 A1* | 6/2011 | Becking ........... A61B 17/12022 606/158 |
| 2011/0152993 A1* | 6/2011 | Marchand ........ A61B 17/12022 623/1.2 |

\* cited by examiner

MESH DISC FOR SACCULAR ANEURYSMS AND COVER FOR SACCULAR OUT-POUCHING

CROSS-REFERENCES

This utility patent application claims the benefit of the priority date of provisional application Ser. No. 62/497,851 filed Dec. 5, 2016 (5 Dec. 2016), and 62/600,134 filed Feb. 13, 2017 (13 Feb. 2017).

FEDERALLY FUNDED R&D

None

BACKGROUND OF THE INVENTION

Field of the Invention

The present disclosure relates to the field of endovascular treatment. More particularly, the present invention uses a modified mesh intrasaccular occlusion device tool, with optional supplemental hydrogel, designed to implement an endovascular treatment to facilitate saccular aneurysm treatment while ameliorating or eliminating the recurrence of aneurysms.

Background Art

Brain aneurysm treatment historically has been the domain of either surgery or, more recently, catheter-placed wire coils. Surgery can be traumatic and expensive, and coils may fail to fully treat an aneurysm.

Saccular aneurysms, also known as berry aneurysms, appear as a round out-pouching and are the most common form of cerebral aneurysm.

Regardless of their size, aneurysms with wide necks are often difficult to treat suitably and safely with traditional endovascular methods. Wide-necked aneurysms are associated with higher incidences of incomplete obliteration, thrombo-embolic events, and parent artery occlusions than are aneurysms with small necks. Recently, a variety of techniques aimed at improving the ability to treat these difficult aneurysms with endovascular methods have been described. Whether these methods use multiple catheters, balloons, or stents, they are all aimed at allowing coils to be positioned and detached in the aneurysm lumen with reduced risk of their herniation into the parent artery.

Intrasaccular flow diverters are increasingly being used in the treatment of wide-neck and bifurcation aneurysms. The present device is structurally distinct from devices described in the prior art for the treatment of intracranial aneurysms.

The present invention is a device for use with an intrasaccular occlusion tool to safely and effectively implement an endovascular treatment of saccular aneurysms while ameliorating or eliminating aneurysm recurrence. The prior art includes endovascular devices have provided high density, mesh-like metallic materials which fill an aneurysm while also crossing the aneurysm neck after forming a cylinder, in place of coil technology.

For example, the Woven EndoBridge device (Web) is a novel device for the treatment of wide-necked intracranial bifurcation aneurysms. As reported by Clajus in J NeuroIntervent Surg (doi:10.1136/neurintsurg-2016-012276) in an article titled "Initial and mid-teen results from 108 consecutive patients with cerebral aneurysms treated with the Web device" the value of webbing generally and Web in particular, was demonstrated when reporting 'real-world experience' in the use of all iterations of Web devices (available in Europe) in ruptured and unruptured aneurysms.

The Luna is another example. The Luna is a self-expandable, multi-layer oval implant made from Nitinol, a nickel-titanium alloy. The properties of the Luna device allow it to easily compress within a conventional catheter, and then rapidly and easily open to full size once deployed within an aneurysm. The Luna is a endosaccular embolization device which is a self-expanding ovoid ball-like implant with a delivery system. The implant is made from a double layer of Nitinol wire mesh secured at both proximal and distal ends and clearly marked with radiopaque platinum markers. A variety of implant diameters is available, as with coils. The delivery system provides distal navigation through a commercially available microcatheter with detachment controlled by operator activation of the delivery handle.

Other references of note include:

U.S. Pat. No. 3,874,388, filed Feb. 12, 1973, published Apr. 1, 1975 Ochsner Med Found Alton Shunt defect closure system;

U.S. Pat. No. 4,282,875, filed Jan. 24, 1979, published Aug. 11, 1981 Serbinenko Fedor A Occlusive device;

U.S. Pat. No. 4,346,712, filed Feb. 13, 1980, published Aug. 31, 1982 Kuraray Company, Ltd., Releasable balloon catheter;

U.S. Pat. No. 4,402,319, filed Dec. 30, 1981, published Sep. 6, 1983 Kuraray Co., Ltd. Releasable balloon catheter U.S. Pat. No. 4,619,246, filed May 20, 1985, published Oct. 28, 1986 William Cook, Europe A/S Collapsible filter basket;

U.S. Pat. No. 4,675,361, filed Jun. 24, 1983, published Jun. 23, 1987 Thoratec Laboratories Corp. Polymer systems suitable for blood-contacting surfaces of a biomedical device, and methods for forming;

U.S. Pat. No. 5,165,421, filed Jul. 20, 1990, published Nov. 24, 1992 Lake Region Manufacturing Co., Inc. Hollow lumen cable apparatus;

U.S. Pat. No. 5,263,963, filed Apr. 8, 1991, published Nov. 23, 1993 Advanced Cardiovascular Systems, Inc. Expandable cage catheter for repairing a damaged blood vessel;

U.S. Pat. No. 5,334,210, filed Apr. 9, 1993, published Aug. 2, 1994 Cook Incorporated Vascular occlusion assembly;

U.S. Pat. No. 5,733,294, filed Feb. 28, 1996, published Mar. 31, 1998 B. Braun Medical, Inc. Self expanding cardiovascular occlusion device, method of using and method of making the same;

U.S. Pat. No. 5,907,893, filed Jan. 31, 1997, published Jun. 1, 1999 Medtronic, Inc. Methods for the manufacture of radially expansible stents;

U.S. Pat. No. 6,221,086, filed May 18, 1999, published Apr. 24, 2001 B. Braun Medical Sas Covered self-expanding vascular occlusion device;

U.S. Pat. No. 6,375,670, filed Aug. 25, 2000, published Apr. 23, 2002 Prodesco, Inc. Intraluminal filter;

U.S. Pat. No. 6,605,102, filed Nov. 12, 1996, published Aug. 12, 2003 Ev3, Inc. Intravascular trap and method of trapping particles in bodily fluids;

U.S. Pat. No. 7,575,582, filed May 16, 2006, published Aug. 18, 2009 Micrus Corporation Apparatus for deployment of micro-coil using a catheter;

US2008/0033341, filed Aug. 6, 2007, published Feb. 7, 2008 Bay Holdings Ltd. Methods and devices for reducing or blocking blood flow to a selected blood vessel or part thereof;

US2010/0069948, filed Sep. 11, 2009, published Mar. 18, 2010 Micrus Endovascular Corporation Self-expandable aneurysm filling device, system and method of placement; and WO2011/057002 A2, filed Nov. 4, 2010, published May 12, 2011 Sequent Medical Inc. Multiple layer filamentary devices or treatment of vascular defects.

The two most frequent ways that web devices fail and thereby result in an aneurysm recur are (1) web device collapse and/or compression and (2) distal migration of the web device into the aneurysm. Additionally, in a ruptured aneurysms there is concern the aneurysm does not close and/or thrombose quickly enough with web devices which has sometimes resulted in recurrent aneurysm rupture after treatment. The present invention is an alternative use for hydrogel intrasaccular occlusion devices is capable of ameliorating said two most frequent web device failure.

The prior art includes "Left atrial appendage occlusion device," WO 2013/126523 A1 (Erzberger et al.), a device known as Watchman. This is a type of left atrial appendage (LAA) closure technology consisting of a delivery catheter and a device that is permanently implanted in the LAA of the heart. This device prevents LAA blood clots from entering the bloodstream and potentially causing a stroke.

The prior art also includes Ser. No. 15/732,147 Hydrogel Intrasaccular Occlusion Device; read and file confirmation for Ser. No. 15/732,365 Alternative Use for Hydrogel Intrasaccular Occlusion Device. However, in the present invention the shape of the device and some other details are quite different. More specifically, the present invention teaches the deployment of a disc across the neck of a saccular aneurism, which is held in place by coils, hydrogel, or other similar materials that fill the body (dome) of the aneurysm, whereas the prior art teaches the deployment of a cylinder which is expanded to conform in shape to the interior surfaces of the target aneurysm.

The prior art teaches various options to treat intracranial aneurysm including craniotomy and clipping, which has significant risk and is quite invasive and requires very for long recovery times, as well as various forms of embolization. The most common form of embolization is coil embolization, which has significant recurrence rates, especially for wide neck aneurysms and larger aneurysms for which the recurrence rates often exceed 20%. In addition, there are options for stent assisted or flow diverting stent techniques. These all involve the use of strong dual antiplatelet such as aspirin and Plavix with their attendant risks, especially in patient presenting with a ruptured aneurysm. Furthermore, treatment of aneurysms with flow diverting devices does not immediately cure the aneurysm. The aneurysm closes over time. The current device seeks to ameliorate these issues by providing a purely intrasaccular treatment option, which limits the need for anti platelets, that bridges wide aneurysm necks and helps prevent coil compaction and aneurysm recurrence.

The prior art also teaches the use of multiple coils to ameliorate saccular aneurysms. One example is known as the TriSpan. The TriSpan is a neck bridge device consisting of three Nitinol loops or "petals"; the proximal ends of these petals are bound together by coiled platinum wire to form a "stem." This stem is then attached to a stainless steel GDC pusher wire measuring 0.014 in. in diameter. A portion of each petal is wrapped with a platinum wire to enhance its radiopacity. During introduction, the TriSpan coil is compressed in a 0.018-in. Tracker 18 catheter. As it is deployed, the loops of the device open like petals on a flower to form a scaffold. Through the same guiding catheter, a second Tracker 18 or a similar catheter with 2 tip markers are then advanced into the aneurysm. Through this catheter, standard Gugliclmi Detachable Coils (GDCs) were placed and detached until the aneurysm was packed as densely as possible. Immediately after detachment of the final GDC, the TriSpan coil was detached.

Compared to the TriSpan, the present invention provides significantly increased aneurysmal neck coverage, which augments flow diversion away from the aneurysm and decreases flow into the aneurysm, while also improving neck coverage to keep any coil loops, hydrogel, or other supplemental intrasaccular fillers from migrating out of the aneurysm and blocking normal parent vessel(s).

Other limitations of the foregoing prior art include, particularly, that the treatment device did not stay in place, was hard to position and did not facilitate preventing compaction. The mesh disc of the present invention overcomes such shortcomings by introducing the structure of a mesh and/or using hydrogel. The prior art, such as TriSpan for instance, teaches away from using a mesh in the material section, in particular by being limited to wire loops.

The present invention is different from stents that have to bridge across the neck of the aneurysm into a vessel past the aneurysm in order to be deployed. The present invention uses a different aneurysm amelioration strategy and structure than does the prior art. The prior art requires crossing the neck of the aneurysm and placing a micro-catheter at a sufficiently distal location in a normal vessel beyond the aneurysm neck, before said stent and/or flow diverter can be deployed. In some aneurysms with difficult anatomy, this maneuver can be difficult, dangerous, and/or impossible. Moreover, they also require leaving a stent in the parent vessel, with the attendant need for dual anti-platelet therapy to prevent in stent-thrombosis, in addition to the risks of in-stent thrombosis and/or in-stent stenosis. The other prior art such as the Web and Luna uses a cylindrical structure that leaves gaps or otherwise does not completely fill the saccular aneurysm. The current invention deploys a combination of the disc and coils, hydrogel, a combination, or other fillers in such a manner as to fill the aneurysm, including non-cylindrical areas. These prior-art devices are also designed as stand-aloneuse devices, without adjunctive hydrogel or coils or other fillers. Furthermore, they have a cylindrical design meant to fit and fill in the majority but not all of the body of the aneurysm. They also do not immediately cure the aneurysm, as thrombosis of the aneurysm may be delayed and/or incomplete.

Additionally, the prior art includes the PulseRider device (PulseRider®). This aneurysm neck reconstruction device is a self-expanding Nitinol implant designed to retain neurovascular embolic coils in un-ruptured wide-necked intracranial aneurysms with neck widths ≥4 mm or dome to neck ratio <2 originating on or near a vessel bifurcation of the basilar tip or carotid terminus with at least a portion of the aneurysm neck overlapping the lumen of the parent artery. The inflow vessels should have diameters from 2.7 mm to 4.5 mm.

The PulseRider is indicated for use with neurovascular embolic coils in patients ≥18 years of age for the treatment of unruptured wide-necked intracranial aneurysms with neck widths ≥4 mm or dome to neck ratio <2 originating on or near a vessel bifurcation of the basilar tip or carotid terminus with at least a portion of the aneurysm neck overlapping the lumen of the parent artery. The inflow vessels should have diameters from 2.7 mm to 4.5 mm. The PulseRider is not indicated for: 1. Patients with vascular anatomy or dimensions at the targeted treatment site for which the available PulseRider sizes are not appropriate; 2. Patients with severe vascular tortuosity or anatomy that would preclude the safe introduction of the PulseRider device; 3. Patients with preoperative coagulation disorder, or with contraindications to antiplatelet or anticoagulant therapy; 4. Patients with known hypersensitivity to nickel; 5. patient with ruptured aneurysms; 6. Patients with side wall aneurysms; and 7. Patients with extra cranial aneurysms. The present invention may be used in each of the seven situations.

The PulseRider is structurally distinct from the present invention because it incorporates elements of a stent with pedals that bridge the aneurysm neck. However, that device is also not within the aneurysm and also requires anti-platelet with its use. The present invention teaches a flat disc like structure designed to be used supplementally with the coils and or hydrogel, or both, or other devices or materials to fill the rest of the aneurysm. The disc is meant to be placed entirely within the aneurysm to minimize the need for antiplatelet that are necessary when devices are placed in the parent vessels.

Additionally, the Web and the Luna utilize radial force on the walls of the aneurysm to become secured in place. Although some of our devices make partial use of this gripping feature for very wide neck aneurysms where there is a portion of the disk that curves up to the walls of the aneurysm, the majority of the mechanism by which our disc is kept in place is by the supplemental coils and/or hydrogel or similar work to secure it in place by pinning the disc against the neck of the aneurysm.

Unlike the prior art, the current invention positioning relies on pinning against the neck of an aneurysm by coils and/or hydrogel or similar, which must be deployed and/or hydrated before the disc is detached. Prior art including The Web and the Luna rely on radial force against the walls of the aneurysm for secure positioning, and which are designed to be stand-alone devices

DESCRIPTION OF THE DRAWINGS

FIG. 3 also depicts an embodiment in which the delivery microcatheter 13 is a microcatheter capable of acting as a conduit for delivery of coils through it.

FIG. 3A also depicts an embodiment in which the delivery microcatheter 13 is a microcatheter capable of acting as a conduit for delivery of coils through it.

DETAILED DESCRIPTION OF THE INVENTION

The present invention can be used with or without hydrogel 16. It should be noted that all hydrogels can optionally expand to a specific external stimulus only, rather than time of hydration. And can potentially shrink to an optional external stimulus. This on-demand expansion and shrinkage is helpful for repositioning medical tools near target areas inside veins and arteries. Said external stimuli include, but are not limited to, thermal, electrical, and/or chemical signals. It should also be noted that hydrogel 16 can optionally be radio-opaque, which facilitates remote locating and positioning of said hydrogel 16.

For the treatment of saccular aneurysms: an endovascularly deployed mesh (metal mesh or other mesh) disc—which will optionally have two layers, like the inner disc of the Anplatz Left Atrial Appendage closure device currently in trials. The disc can have versions that are relatively flat, or some versions where the edges are folded up to accommodate differently shaped aneurysms, including very wide neck aneurysms. Such deviations from the generally flat plane of the mesh disc 14 of the current invention may have turned-up sides which conform to the walls of a target aneurysm 100 which are proximal to the aneurysmal neck. Said upturned elements 14A (sometimes referred to as "lips") are optional and optimally used for very wide neck aneurysms that are less spherical in shape and more cylindrical in shape. With said more wide neck aneurysms the anatomy does not lend itself to the deployment of a flat mesh disc because wide neck aneurysms lack sufficient overhang regions at the neck to support the mesh disc. Without such support said mesh disc will be dislodged into the parent artery. The present invention teaches the use of multiple distinct lip configurations. The lip configurations differ in diameter, shape and orientation. In the preferred embodiment the central portion of the mesh disc (i.e. the portion closest to the delivery element, such as the wire or deliver microcatheter) will be oriented parallel to the neck of the target aneurysm.

The diameter of the mesh disc ranges from 0.1 mm to 30 cm.

The shape of the mesh disc ranges from a circle to triangle. The shape is most typically round or oval.

In a typical spherical aneurysm with a narrow neck, the entire mesh disc, include the lips, should be oriented parallel to the neck of the target aneurysm. In this case, the lips overhang and rest on the base of the target aneurysm, completely covering the neck of the target aneurysm and extending over a portion of the adjacent base of the target aneurysm.

In a typical non-spherical aneurysm with a wide neck, the entire outer perimeter of the mesh disc should be oriented more perpendicular to the neck of the target aneurysm than in the case of the typical spherical aneurysm with a narrow neck, so as to gently grip the walls near the base of the target aneurysm.

Figure 1:
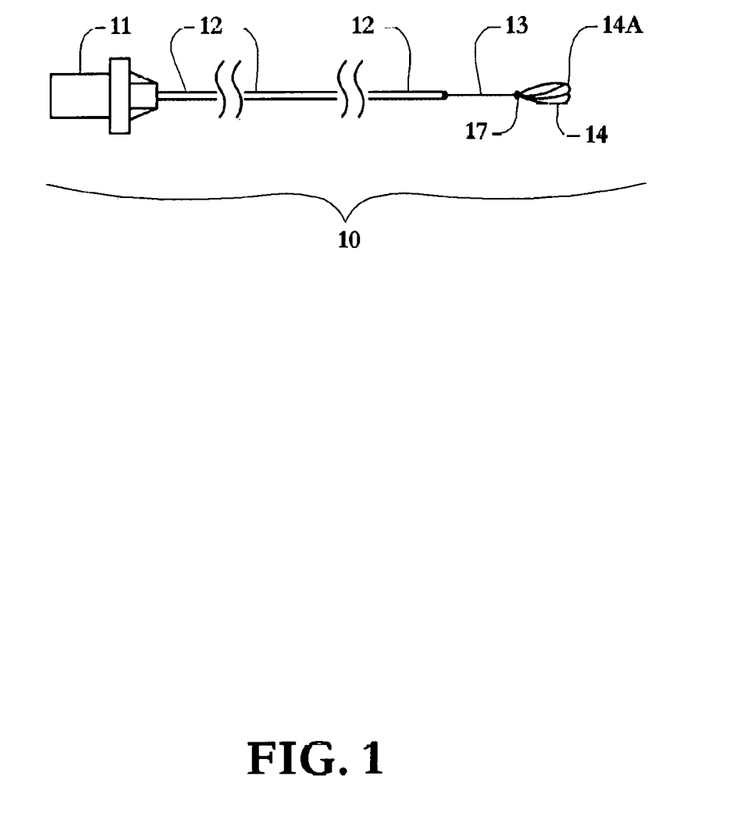
FIG. 1 depicts the present invention 10, including control element 11, catheter element 12 (in cutaway), delivery microcatheter element 13, detachment element 17, and a compressed, flexible mesh disc 14 with peripheral lips 14A, suitable for delivery through microcatheter element 13 and expanded upon release from constraint.

Referring now to FIG. 1, control element 11 is the user interface that has the optional capability of sending signals through catheter element 12, sometimes termed delivery catheter 12, and/or along delivery microcatheter 13, sometimes termed a hypotube 13. In some cases the "microcatheter" 13 may be solid (such as when microcatheter 13 is a wire). Control element 11 is deployed outside the body containing the target aneurysm. Control element 11 optionally deploys catheter 12 to a location proximal to the base of the neck of the target aneurysm 100. Said control element 11 is optionally attached to catheter element 12 and/or optionally attached to delivery microcatheter 13 disposed therein. Said control element 11 is capable of sending signals via catheter element 12 and/or delivery microcatheter 13 to detachment element 17. In the preferred embodiment control element 11 is a separate detachment tool that is applied to the proximal side of delivery microcatheter 13 at the desired time, in order to detach the mesh disc 14 from said delivery microcatheter 13. Prior to deployment, additional contrast or other fluid injections can optionally be used to initiate deployment of optional ballon(s) 303 or 300 for the purpose of positioning catheter 12 so as to center delivery microcatheter 13 for optimal deployment of mesh disc 14. Detachment element 17 in turn may relay signals to mesh disc element 14. Said relay signals are capable of initiating the decompression of said disc 14 upon deployment. Alternatively, said compression may be automatic triggered by its release from constraints. Following deployment of mesh disc 14, control element 11 is optionally capable of sending signals which result in the deployment of coils 24, hydrogel 16, and/or lips 14A. In the preferred embodiment a separate control element 20 controls detachment of coils 24. Following deployment of the aforementioned elements, control element 11 is capable of signaling detachment element 17 to separate delivery microcatheter 13 from mesh disc 14. Control element 11 is then capable of retracting catheter 12 and delivery microcatheter 13. In the preferred embodiment, the control element 11 is commercially available.

In the preferred embodiment catheter 12 has an outer diameter ranging from 3Fr. to 5Fr.

Note that the mesh disc 14 will be held in position upon deployment by coils 24 or hydrogel 16, each of which will substantially conform to the interior of target aneurysm 100. Alternatively, mesh disc 14 must have up going "lips" and can be held in place by friction between said disc and the walls of the target aneurysm, as well as the fact that disc 14 has a greater diameter than the diameter of the aneurysmal neck. Lastly, a larger disc 14 can be held in place both ways.

Mesh disc 14 is compressible into a shape suitable for delivery through a catheter 12, and capable of expanding into a disc shape upon receipt of an electronic signal from control element 11, or upon release from its constraint. Said mesh 14 is capable of being coated with hydrogel 16, and holes in said mesh 14 are capable of storing said hydrogel 16 until deployment within said aneurysm 100.

The amount of said hydrogel 16 may vary. The specific amount is not significant so long as sufficient hydrogel 16 is deliverable to the aneurysm 100 to fill it. Typically, the smallest volume is approximately equivalent to a 3 mm sphere; the largest is approximately equivalent to an 8 mm sphere. In the preferred embodiment of the present invention the optional hydrogel coats mesh disc 14 such that the hydrogel will expand into and filling the aneurysm dome.

Mesh disc 14 is releasably attached to delivery microcatheter 13 by detachment element 17.

Mesh disc 14 in the preferred embodiment is radio-opaque or has radio-opaque marker or other positioning markers or incorporates other technology for remote visualization and location detection. The same characteristic are incorporated in detachment element 17.

Figure 2:
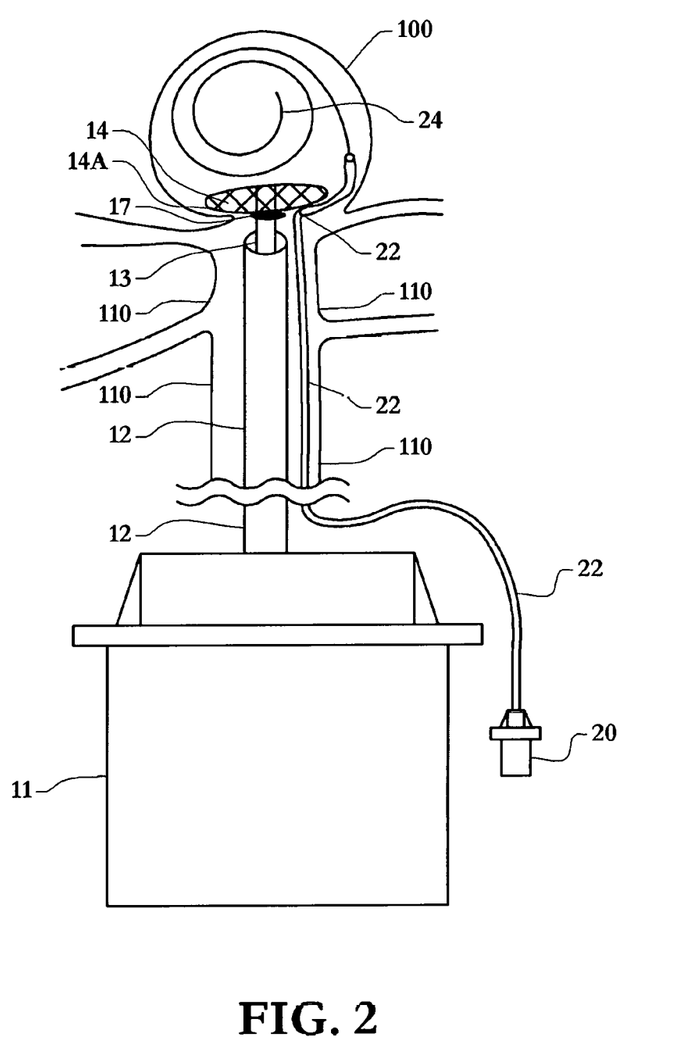
FIG. 2 depicts lips element 14A at periphery of flexible, substantially flat mesh disc 14 when uncompressed following delivery through and release from microcatheter 13 (said microcatheter 13 may be a solid wire, a microcatheter or a combination thereof) disposed within aneurysmal neck 100; along with a deployed prior art device composed of control element 20, catheter 22, and wire coil 24 introduced into saccular aneurysm 100.

Referring now to FIG. 2, the mesh disc 14 is deployed through delivery catheter 12 passing through vessel 110 to the base of the neck of target saccular aneurysm 100. Control device 11 may optionally signal delivery microcatheter 13 to extend beyond the distal end of catheter 12 in a length sufficient to enter target aneurysm 100 to allow deployment of mesh disc 14. Once the progress of delivery microcatheter 13 ceases, control element 11 signals mesh disc 14 to deploy. Mesh disc 14 enters the target aneurysm in a compacted form, said signal from control element 11 directs said mesh disc 14 to open as a blossom to allow the perimeter of said disc 14 to overlap the base of the neck of the aneurysm 100. In the preferred embodiment the delivery catheter 12 is manually held in place while the delivery microcatheter 13 is manually advanced forward in a length sufficient to enter target aneurysm 100 to allow deployment of mesh disc 14. Mesh disc 14 enters the target aneurysm in a compacted form and as it is released from its constraint said mesh disc 14 opens as a blossom to allow the perimeter of said disc 14 to overlap the base of the neck of the aneurysm 100. The disc is then gently pulled back manually into position, which is determined preferentially by fluoroscopic and/or angiographic images.

The present invention employs a control element 11. Said control element's function is to detach mesh disc 14 at a specific time. Control element 11 may be combined with control elements of various devices which may be used with the present invention. Control element 11 may incorporate mechanical, chemical, hydrostatic, electrical and/or thermal means for implementing the function of detaching mesh disc 14.

Continuing to refer to FIG. 2, such deployment can accompany the deployment of existing devices which disrupt the flow across the aneurysmal neck, such as prior art coil 24 in the saccular aneurysm as illustrated in FIG. 2 deployed by a second control element 20 through second catheter 22. It should be noted that mesh disc element 14 of the present invention is capable of resulting in a second "jailed" microcatheter.

Figure 3:
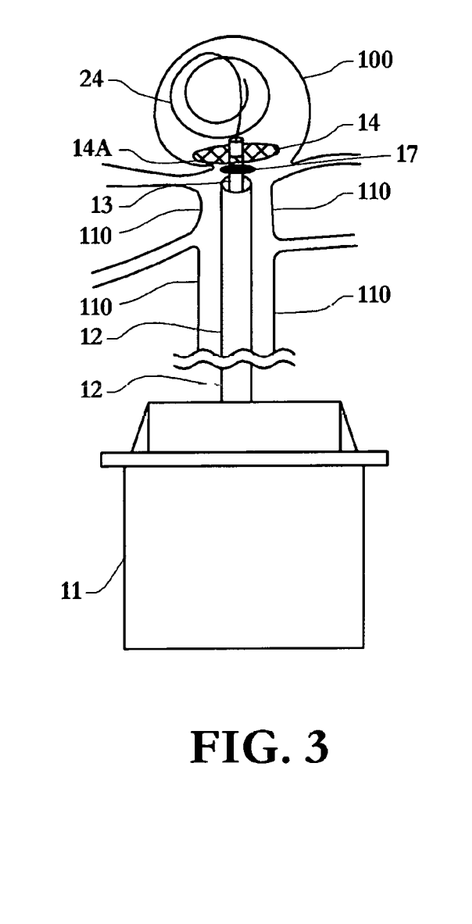
FIG. 3 depicts the present invention 10 deployed through vessel 110 with mesh disc 14 deployed at base of neck of a target spherical aneurysm 100, integrating wire coil element 24 of the prior art.

Referring now to FIG. 3, the present invention may incorporate elements of the prior art, such as the deployment of coils 24 through microcatheter 13.

Figure 3A:
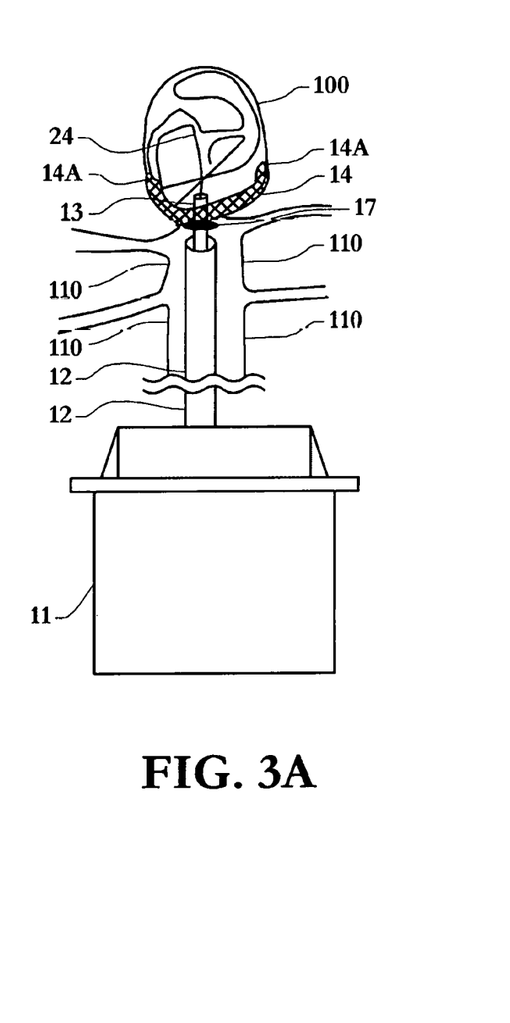
FIG. 3A depicts the present invention 10 deployed through vessel 110 with mesh disc 14 deployed at base of neck of target non-sperical aneurysm 100, integrating wire coil element 24 of the prior art.

Referring now to FIG. 3A, the present invention teaches the use of up turned lips to secure said mesh disc.

Figure 4:
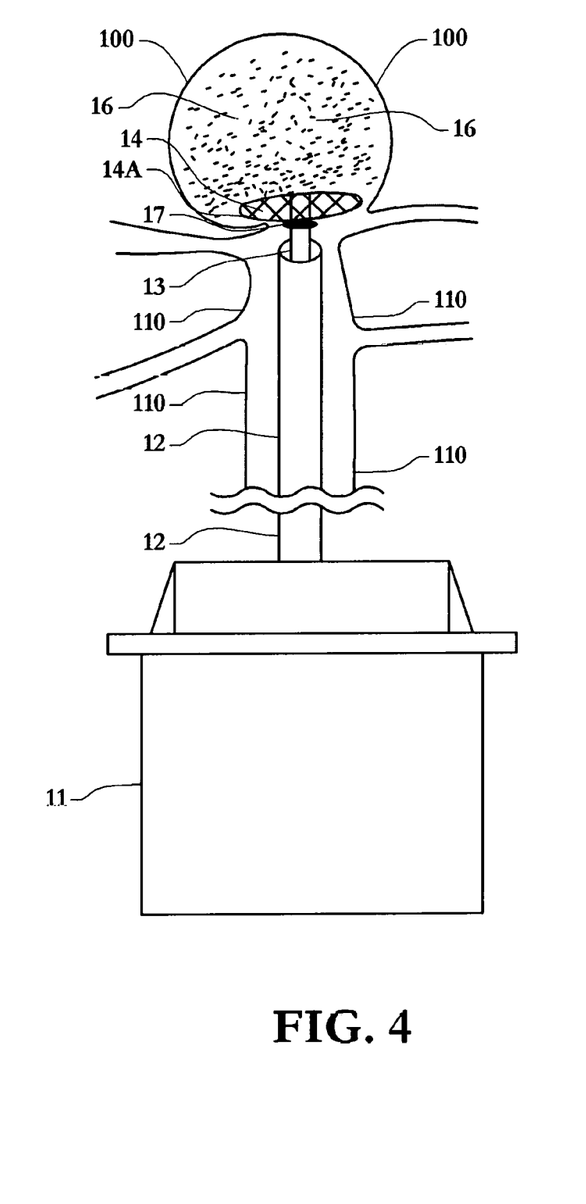
FIG. 4 illustrates an alternate embodiment of the present invention, deploying activated (swollen) hydrogel 16 within target aneurysm 100.

Referring now to FIG. 4, an alternate embodiment of the present invention deploys mesh disc 14 in conjunction with semitransparent, activated/swollen hydrogel 16. Hydrogel 16 can be deployed on the surface of mesh disc 14, via a hollow in delivery microcatheter 13, via a second device (not shown), or via a second wire (not shown) deployed through catheter element 12. Alternatively, the hydrogel 16 may be deployed via the mesh disc 14. Alternatively, hydrogel embedded coils may be used with the present invention.

Figure 5:
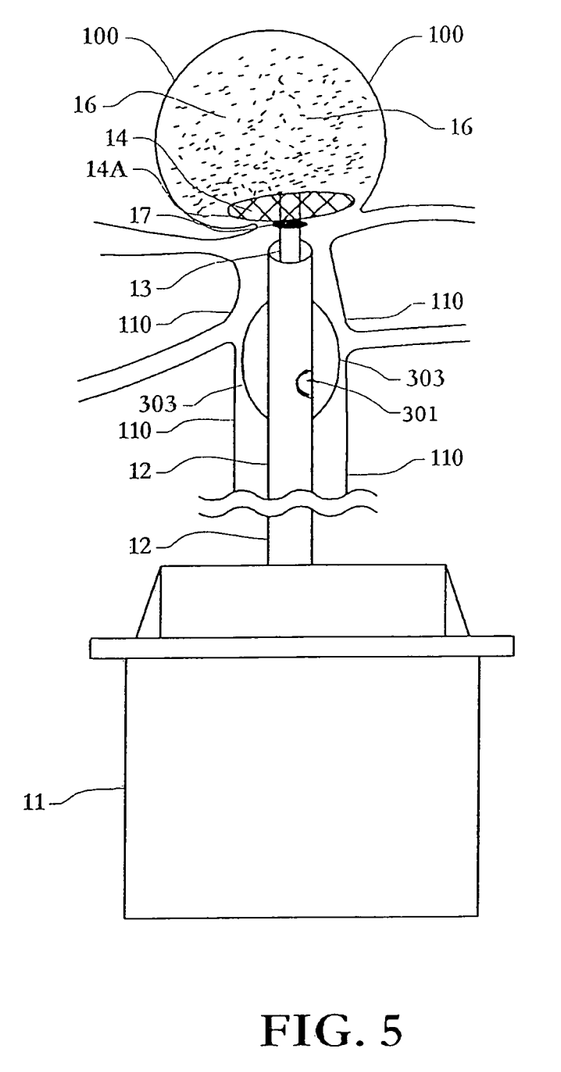
FIG. 5 depicts an alternate embodiment of FIG. 4, further including at least one side hole 301 optional centering balloon 303 to position catheter element 22 more precisely in relation to the center of the neck of target aneurysm 100.

Referring now to FIG. 5, an alternate embodiment of FIG. 4 further includes a centering balloon 303 within vessel 110. Centering balloon 303 is deployed through at least one side hole 301 allowing catheter element 12 to be positioned more precisely and stably in relation to the center of the neck of target aneurysm 100. Referring more particularly to centering balloon 303, said balloon is described in detail in Walzman application Ser. No. 15/482,436 (titled Vessel access catheter), incorporated herewith by reference.

It should be noted that Walzman application Ser. No. 15/482,436 (titled Vessel access catheter), incorporated herewith by reference describes both single balloons and balloon arrays. The present invention's centering balloon 303 may be either a single balloon or a balloon array. Said single balloon or balloon arrays are designed to help center the tip of catheter element 12 to a location proximal to the center of the target aneurysm. Said positioning may be achieved by the inflation of at least one balloon in order to deflect catheter element 12 in a desired direction.

Figure 6:
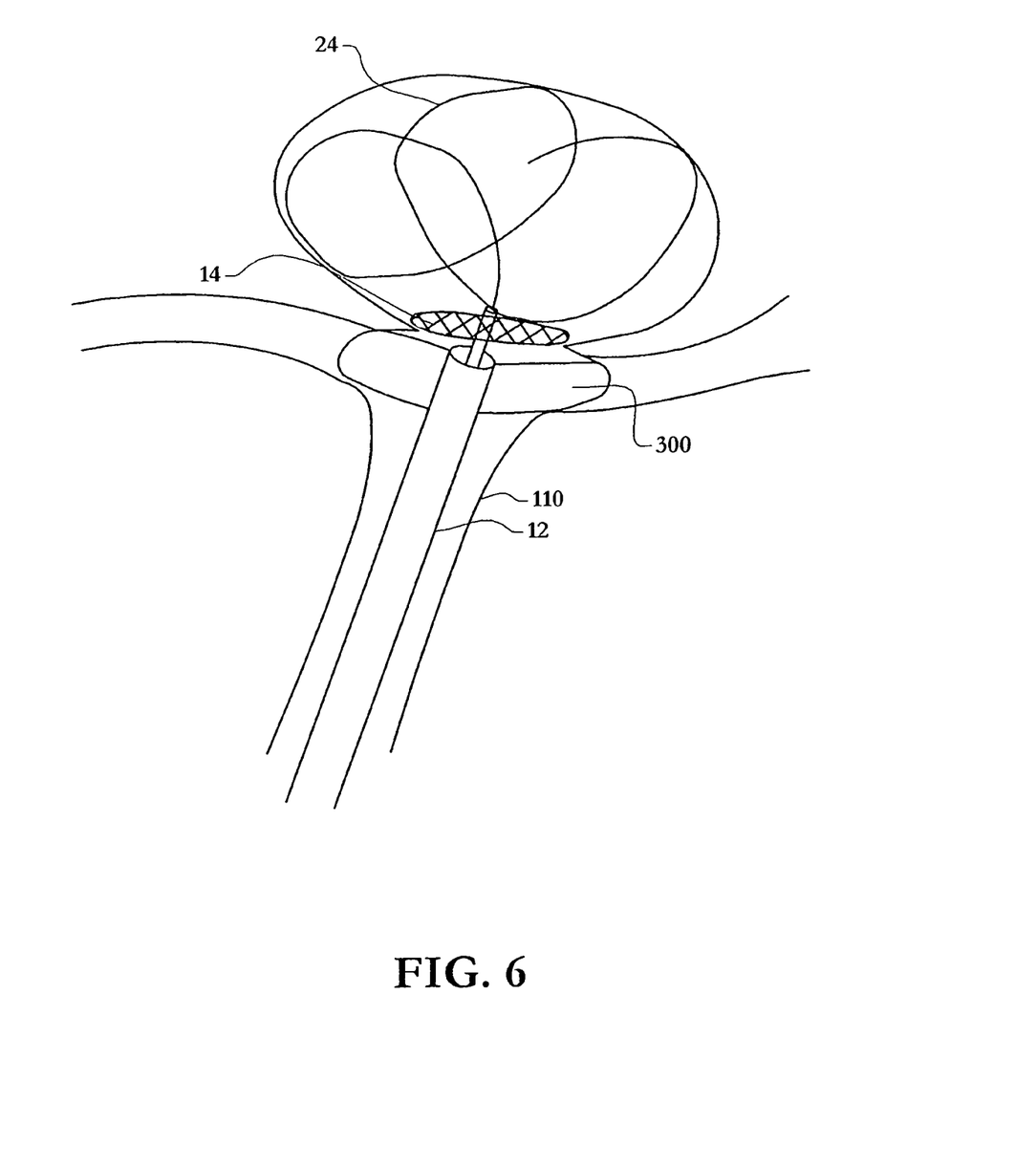
FIG. 6 illustrates a detailed deployment of the optional disc balloon 300.

An additional embodiment of the current invention incorporates the Walzman disc balloon 300, as illustrated by FIG. 6, into catheter element 12. Said incorporation is an alternate embodiment which is designed to help center the tip of catheter element 12 to a location proximal to the center of the target aneurysm. It may also act as vertical positioning element by abutting the base of the mesh disc during positioning in the target aneurysm.

Both balloon embodiments separately or in combination are also designed to arrest flow within the vessel proximate to the target aneurysm when fully inflated. Said inflation will result in control of unwanted bleeding in case of target aneurysm rupture.

Thus, the present invention can have several different embodiments, including:

(1) Disc alone—an appropriately sized disc can be deployed through a microcatheter in a saccular aneurysm, after a second microcatheter is placed in the microcatheter. The disc is gently pulled back to the neck of the aneurysm, bridging said neck, and with a lip beyond the open portion of the neck to stabilize the disc. The disc is not detached at first, but remains tethered to its delivery system (a wire or catheter). Were it to be deployed early it would likely migrate into the aneurysm and be ineffective and sometimes dangerous. Through the second microcatheter, which is now "jailed" in the aneurysm, appropriately sized coils are sequentially placed and deployed into the aneurysm per current routine protocols/techniques, until the aneurysm is adequately filled with coils. The second microcatheter is removed. At this point the disc is detached from its delivery wire/catheter, which is removed.

(2) Disc mounted on a hypotube or microcatheter 13 which is introduced into aneurysm through a slightly larger catheter, wherein the hypotube or microcatheter goes through the disc to just beyond it. An appropriately sized disc can be deployed through a microcatheter in a saccular aneurysm. The disc is gently pulled back to the neck of the aneurysm, bridging said neck, and with a lip beyond the open portion of the neck to stabilize the disc. The disc is not detached at first, but remains tethered to its delivery catheter/hypotube. Were it to be detached early it would likely migrate into the aneurysm and be ineffective and sometimes dangerous. Through said delivery catheter/microcatheter appropriately sized coils are sequentially placed and deployed into the aneurysm per current routine protocols/techniques, until the aneurysm is adequately filled with coils. At this point the disc is detached from its catheter/hypotube. The catheter/hypotube is then removed.

(3) Hydrogel enhanced disc alone—The disc is an endovascularly deployed mesh composed of a shape-memory material such as nickel-titanium alloy or other memory-shape material capable of super-elastic properties, such that the compressed mesh disc will revert to its flat-mesh disc shape upon release or activation by an electronic or light impulse. It will optionally have two layers like to inner disc of the Anplatz Left Atrial Appendage closure device currently in trials—the disc can have versions that are relatively flat, or some versions where the edges are folded up to accommodate different shape aneurysms, including very wide neck aneurysm. In this version, however, the outside surface of the disc facing into the aneurysm is lined with a non-biodegradable hydrogel, that when exposed to blood upon deployment, will swell over a prescribed time (10 minutes in the preferred embodiment of the present invention), to conform to the size and shape of the aneurysm, and fill and occlude said aneurysm. The other layer of the disc that is closer to the parent artery can optionally have thin layers of hydrogel as well—but this layer would have hydrogel designed only to swell to occlude that layer of disc alone, so no hydrogel from the other layer can potentially expand through the mesh into the parent vessel. An appropriately sized disc can be deployed through a microcatheter in a saccular aneurysm. The disc is gently pulled back to the neck of the aneurysm, bridging said neck, and with a lip beyond the open portion of the neck to stabilize the disc. The disc is not detached at first, but remains tethered to its delivery system (a wire or catheter). Were it to be detached early it would likely migrate into the aneurysm and be ineffective and sometimes dangerous. The disc is held in place at the neck of the aneurysm, while the hydrogels swell. Once the prescribed time is elapsed and follow up angiography confirms occlusion of the aneurysm, the disc is detached from its delivery wire/catheter, and the delivery wire/catheter and the microcatheter through which it was deployed are removed. The hydrogel fills the aneurysm, which occludes that aneurysm and also stabilizes the disc in place (in example 1 and 2 above the coils achieve these 2 goals)

(4) All features of 1, 2, and 3 optionally; plus the disc can have a smaller metal core disc that is smaller than the diameter of the aneurysm and has hydrogel designed to expand out in a disc like shape from the edges, to make a larger disc that can then be gently dragged into position. It can then be pinned in place by coils or optional hydrogel embedded in the top of the disc, that also then expands into the dome of the aneurysm, either via a layer on the top of the metal disc designed to expand after the side hydrogel, or via a separately implanted hydrogel bead or the like.

(5) Instead of the metal disc that expands in diameter via hydrogel, you can have an all hydrogel disc on a pusher wire or hypotube/catheter, and expands in a flat disc shape to various pre-programmed diameters and/or shapes.

The disc may also optionally be delivered through a disc balloon microcatheter (previously described by Walzman Ser. No. 15/732,170) or a similar configuration (disc balloon) intermediate catheter, or another balloon catheter. This can be a method for delivering the present invention. Said method may also be used to deliver any mesh intrasaccular device including other devices taught by the prior art, such as the Web and the Luna.

The advantage of a delivery through a disc balloon microcatheter is twofold. First, the balloon may sometimes be helpful positioning the disc and second, that in the event the aneurysm ruptures during treatment, the balloon can be inflated to arrest flow and control active bleeding until more coils can be placed and/or the hydrogel swells to seal the aneurysm.

Although the invention has been described in detail in the foregoing embodiments for the purpose of illustration, it is to be understood that such detail is solely for that purpose, and that variations can be made therein by those skilled in the art without departing from the spirit and scope of the invention, except as it may be described by the following claims.

What is claimed is:

1. An embolic device for ameliorating bodily outpouchings, comprising
    a control element,
    a catheter element,
    a delivery microcatheter hypotube,
    a detachment element,
    a mesh disc,
    a distal opening,
    at least one side hole,
    and at least two centering balloons deployed via said at least one side hole to position said catheter element in relation to the center of a target aneurysmal neck,
    wherein said mesh disc further comprises a proximal face and a distal face, said proximal face being opposite of said distal face;
    said proximal face and said distal face are substantially flat; and
    wherein said mesh disc upon deployment is disposed distally is configured to be in communication with said target aneurysmal neck;
    wherein said mesh disc further comprises peripheral lips configured to be oriented parallel to said aneurysmal neck,
    wherein said peripheral lips are configured to overhang and rest on a base of said target aneurysmal neck.

2. The device of claim 1, wherein said mesh disc is flexible.

3. The device of claim 1, wherein said mesh disc is capable of deploying hydrogel in a sufficient amount to fill said outpouchings.

4. The device of claim 3, wherein said hydrogel is delivered through said delivery hypotube for deployment by said mesh disc.

5. The mesh disc according to claim 1, wherein said mesh disc is at least 4 mm in width.

6. The device of claim 5, further comprising adhered hydrogel.

7. The device of claim 1, further comprising adhered hydrogel.

8. An embolic device for ameliorating bodily outpouchings, comprising a control element, a catheter element, a wire, a detachment element, a mesh disc, a distal opening, at least one side hole, and at least two centering balloons deployed via said at least one side hole to position said catheter element in relation to the center of a target aneurysmal opening:
    wherein said mesh disc further comprises proximal face and a distal face,
    said proximal face being opposite of said distal face;
    and said proximal face and said distal face are substantially flat,
    wherein said mesh disc upon deployment is disposed distally and is configured to be in communication with said aneurysmal opening;
    wherein said mesh disc further comprises peripheral lips configured to be oriented parallel to said aneurysmal opening,
    wherein said peripheral lips are configured to overhang and rest on a base of said target aneurysmal neck.

9. The device of claim 8, wherein said mesh disc is flexible.

10. The device of claim 8, wherein said mesh disc is capable of deploying hydrogel in a sufficient amount to fill said outpouching outpouchings.

11. The device of claim 8, wherein said mesh disc further comprises hydrogel, wherein said mesh disc is impregnated with said hydrogel in a sufficient amount to substantially fill said outpouching outpouchings.

12. The device of claim 8, wherein a periphery of said mesh disc is upturned.

13. The device of claim 8, wherein said mesh disc is positioned at the neck of said outpouching outpouchings.

14. The device of claim 13, wherein said mesh disc does not substantially fill said outpouching outpouchings.

15. The device of claim 1, wherein said mesh disc further comprises hydrogel, wherein said mesh disc is impregnated with said hydrogel in a sufficient amount to substantially fill said outpouching outpouchings.

16. The mesh disc according to claim 8, wherein said mesh disc is at least 4 mm in width.

17. The device of claim 16, further comprising adhered hydrogel.

18. The device of claim 8, further comprising adhered hydrogel.

* * * * *